(12) United States Patent
Brandl et al.

(10) Patent No.: US 9,345,454 B2
(45) Date of Patent: May 24, 2016

(54) CINE-LOOP ADJUSTMENT

(71) Applicant: General Electric Company, Schenectady, NY (US)

(72) Inventors: Helmut Brandl, Zipf (AT); Erwin Fosodeder, Zipf (AT)

(73) Assignee: General Electric Company, Schenectady, NY (US)

(*) Notice: Subject to any disclaimer, the term of this patent is extended or adjusted under 35 U.S.C. 154(b) by 43 days.

(21) Appl. No.: 14/509,810

(22) Filed: Oct. 8, 2014

(65) Prior Publication Data

US 2016/0100823 A1  Apr. 14, 2016

(51) Int. Cl.
| | | |
|---|---|---|
| *G06K 9/00* | (2006.01) | |
| *A61B 8/08* | (2006.01) | |
| *A61B 8/02* | (2006.01) | |
| *H04N 5/232* | (2006.01) | |
| *G06T 7/00* | (2006.01) | |
| *G06T 5/00* | (2006.01) | |

(52) U.S. Cl.
CPC .............. *A61B 8/5276* (2013.01); *A61B 8/02* (2013.01); *A61B 8/488* (2013.01); *A61B 8/5284* (2013.01); *G06T 5/002* (2013.01); *G06T 7/0038* (2013.01); *H04N 5/23229* (2013.01); *G06T 2207/10132* (2013.01); *G06T 2207/30048* (2013.01)

(58) Field of Classification Search
USPC ........................................................ 382/131
See application file for complete search history.

(56) References Cited

U.S. PATENT DOCUMENTS

| | | | | |
|---|---|---|---|---|
| 5,588,434 | A * | 12/1996 | Fujimoto | A61B 8/12 600/443 |
| 7,142,633 | B2 | 11/2006 | Eberhard et al. | |
| 7,248,725 | B2 | 7/2007 | Zwirn et al. | |
| 7,676,091 | B2 | 3/2010 | Zwirn et al. | |
| 2004/0024306 | A1* | 2/2004 | Hamilton | A61B 5/055 600/410 |
| 2004/0143189 | A1* | 7/2004 | Lysyansky | A61B 8/08 600/450 |
| 2006/0079790 | A1* | 4/2006 | Kuth | A61B 5/055 600/478 |
| 2010/0195881 | A1* | 8/2010 | Orderud | A61B 8/08 382/131 |
| 2014/0128738 | A1* | 5/2014 | White | A61B 8/0883 600/447 |
| 2014/0243650 | A1* | 8/2014 | Oren | A61B 5/064 600/407 |
| 2015/0190112 | A1* | 7/2015 | Yeo | A61B 8/0866 600/443 |

OTHER PUBLICATIONS

Spooner, How to make a Cool Cinemagraph Image in Photoshop, Feb. 18, 2013, published on http://blog.spoongraphics.co.uk/tutorials/how-to-make-a-cool-cinemagraph-image-in-photoshop.*

* cited by examiner

*Primary Examiner* — John Strege

(57) ABSTRACT

Techniques for imaging adjusting a cine-loop are described herein. A cine-loop may be generated, and it may be identified whether the cine-loop has a stitching artifact. The cine-loop may be played, and the length of the cine-loop may be adjusted while the cine-loop is playing until the stitching artifact is substantially removed.

20 Claims, 6 Drawing Sheets

200

300

400

500

CINE-LOOP ADJUSTMENT

BACKGROUND OF THE INVENTION

The subject matter disclosed herein relates generally to techniques for diagnostic medical imaging, such as ultrasound medical imaging. In diagnostic medical imaging, systems may be configured to capture images of a subject. In some cases, diagnostic imaging may enable multiple images to be captured at a high frame rate. Multiple images captured at a high frame rate sequentially displayed may be viewed as a video. In some cases, a cine-loop may be generated. A cine-loop is video wherein an end frame of a video may be stitched to a beginning frame of a video such that the video may be played over again in a sequential loop for a desired number of iterations. In some scenarios, stitching frames according to a period of a moving imaged object may be difficult, and may generate a stitching artifact wherein the end frame does not coincide with an end of the period of the moving imaged object.

BRIEF DESCRIPTION OF THE INVENTION

An embodiment relates to a method for adjusting a cine-loop. The method includes generating a cine-loop and identifying whether the cine-loop has a stitching artifact. If the cine-loop includes a stitching artifact, the cine-loop is played. A length of the cine-loop is adjusted while the cine-loop is playing until the stitching artifact is substantially removed.

Another embodiment relates to a system adjusting a cine-loop. The system includes a processing device and an adjustment module. The adjustment module is configured to generate a cine-loop. It may be identified whether the cine-loop has a stitching artifact. If the cine-loop includes a stitching artifact, the cine-loop is played. A length of the cine-loop is adjusted while the cine-loop is playing until the stitching artifact is substantially removed.

Still another embodiment relates to a computer-readable medium adjusting a cine-loop. The computer-readable medium includes processor-executable code to generate a cine-loop. The computer-readable medium generates the cine-loop by automatically determining a length of the cine-loop to substantially remove a stitching artifact.

BRIEF DESCRIPTION OF THE DRAWINGS

The present techniques will become more fully understood from the following detailed description, taken in conjunction with the accompanying drawings, wherein like reference numerals refer to like parts, in which.

DETAILED DESCRIPTION OF THE INVENTION

Figure 1:
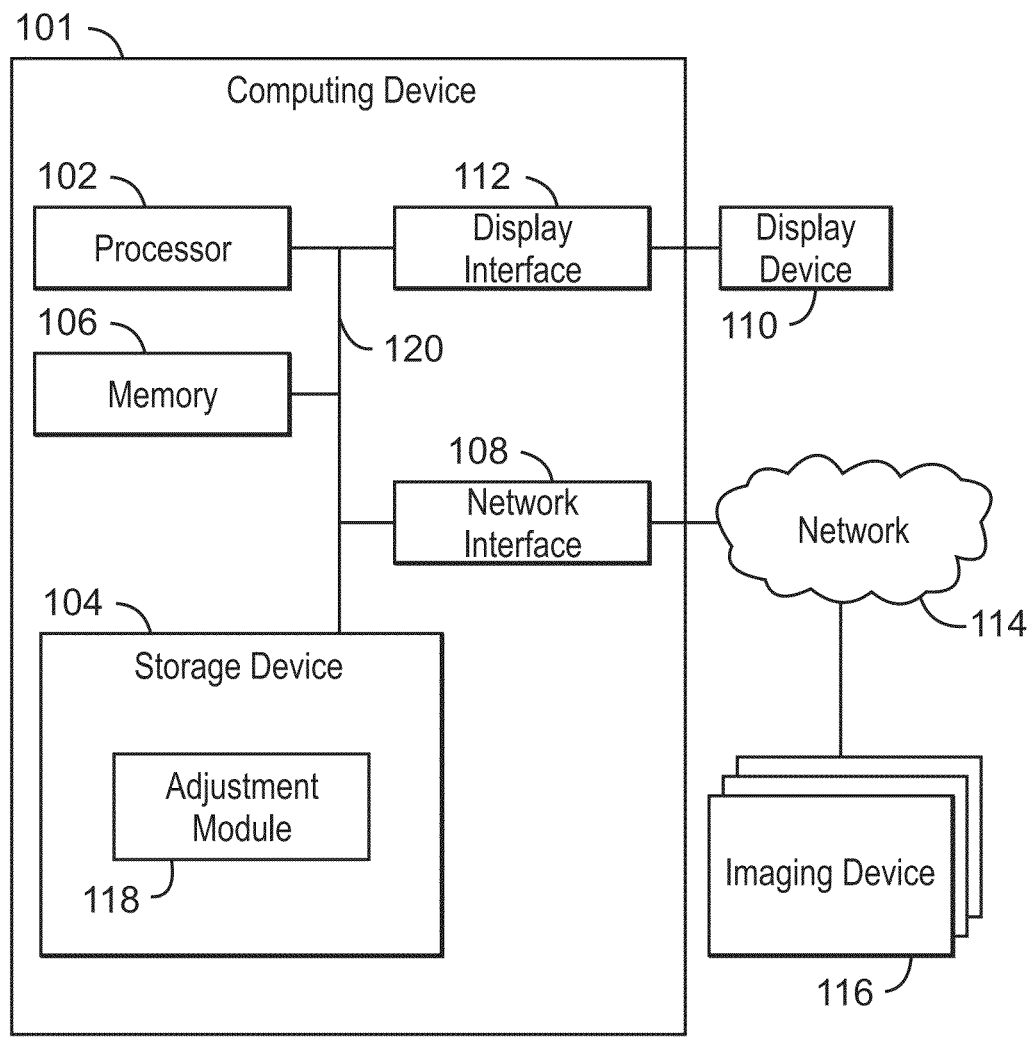
FIG. 1 illustrates a block diagram illustrating a computing system configured to adjust a cine-loop.

In the following detailed description, reference is made to the accompanying drawings that form a part hereof, and in which is shown by way of illustration of specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the embodiments described herein.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. Various modules or units shown in the attached figures may represent the hardware that operates based on software or hardwired instructions, the software that directs hardware to perform the operations, or a combination thereof.

Various embodiments provide techniques for adjusting a cine-loop. As discussed above, a cine-loop is a sequence of frames that are stitched together based on a period of a moving object. In the embodiments discussed herein, the object is a heart, such as a fetal heart. However, other objects may be used.

In embodiments, the images are captured in two dimensions such as a snapshot image, two dimensions with Doppler image data, four dimensions, four dimensions having Doppler image data, and the like. For example, images of a given cine-loop may be three-dimensional wherein the fourth dimension is a period of time. In other words, the embodiments discussed herein may be used on three-dimensional image data captured over a period of time. Each three-dimensional image may be referred to herein as a volume. Changes of a volume over time represent a four-dimensional image capture. As discussed above, a user may wish to capture one cycle of a periodically moving object, and create a loop that may continue for a desired amount of time for analysis of the cycle. For example, a heartbeat may occur once for a given time period. A user, such as a physician, a medical technician, and the like, may desire to review one heart beat over and over for a desired amount of time to determine health aspects of the heart. However, in some cases, it may be difficult to capture a single heartbeat without including too much data, wherein more than one heartbeat is captured in the cine-loop, or by including too little data, wherein less than one full heartbeat is captured in the cine-loop. Including too much data, or too little data, may result in a stitching artifact wherein images of the cine-loop will appear to jump as the cine-loop nears the end of the cine-loop and begins again at a selected start frame.

The techniques described herein include adjusting a cine-loop length while the cine-loop is playing. The adjustment of the cine-loop length while the cine-loop is playing allows a user to select a length that substantially reduces or removes a stitching artifact. For example, the cine-loop may be a four dimensional ultrasound of a fetal heart. As the fetal heart beats quickly, the ultrasound may be configured to capture four dimensional data at a fast rate to produce a cine-loop. To generate an initial cine-loop, a user may select a starting volume indicating a systole position of the heart. An end frame may be selected initially based on a predetermined average period of one heartbeat for a fetal heart. However, the initial cine-loop may contain a stitching artifact as the actual period of the fetal heartbeat may be faster or longer than the predetermined average. Therefore, while the cine-loop is playing, a user may adjust the cine-loop length to substantially remove the stitching artifact.

It should be noted that although the various embodiments are described in connection with a particular diagnostic medical imaging system, such as an ultrasound, embodiments may be implemented in connection with other imaging systems implementing cine-loop analysis Additionally, the imaging system may be used to image different objects, including objects other than people. Further, although the techniques described herein refer to four dimensional imaging, other types of dimensional imaging may be used, wherein the techniques described herein reduce stitching artifacts of a cine-loop.

FIG. 1 illustrates a block diagram illustrating a computing system configured to adjust a cine-loop. The computing system 100 may include a computing device 101 having a processor 102, a storage device 104, a memory device 106, a network interface 108, a display device 110, and a display interface 112. The computing device 101 may communicate, via the network interface 108, with a network 114 to access a one or more imaging devices 118.

The storage device 104 may be a non-transitory computer-readable medium having an adjustment module 118. In some cases, the adjustment module 118 may include code that is executable by the processor 102. In some cases, the adjustment module 118 may be implemented as logic, at least partially comprising hardware logic, as firmware embedded into a larger computing system, or any combination thereof. The adjustment module 118 is configured to generate a cine-loop and identify whether the cine-loop has a stitching artifact. In some cases, the identification may be performed by a user via a human input device (HID), such as a mouse, a keyboard, and the like. The user input may be received by the adjustment module 118. In any case, the cine-loop having the stitching artifact may be played. A length of the cine-loop is adjusted until the stitching artifact is substantially removed. In some cases, the adjustment may be performed via user input and may be received by the adjust module 118. In other cases, the adjustment may be performed by the adjustment module 118 by identifying a period associated with movements of the captured images. In this case, the adjustment may be performed by the adjustment module 118 automatically, as discussed in more detail below in regard to FIG. 6.

The processor 102 may be a main processor that is adapted to execute the stored instructions. The processor 102 may be a single core processor, a multi-core processor, a computing cluster, or any number of other configurations. The processor 102 may be implemented as Complex Instruction Set Computer (CISC) or Reduced Instruction Set Computer (RISC) processors, x86 Instruction set compatible processors, multi-core, or any other microprocessor or central processing unit (CPU), or graphic processing unit (GPU).

The memory device 106 can include random access memory (RAM) (e.g., static RAM, dynamic RAM, zero capacitor RAM, Silicon-Oxide-Nitride-Oxide-Silicon, embedded dynamic RAM, extended data out RAM, double data rate RAM, resistive RAM, parameter RAM, etc.), read only memory (ROM) (e.g., Mask ROM, parameter ROM, erasable programmable ROM, electrically erasable programmable ROM, etc.), flash memory, or any other suitable memory systems. The main processor 102 may be connected through a system bus 120 (e.g., PCI, ISA, PCI-Express, etc.) to the network interface 108. The network interface 108 may enable the computing device 101 to communicate, via the network 114, with on or more imaging devices 116. Although not illustrated in FIG. 1, in embodiments, the computing device 101 may be directly connected to one or more imaging devices, such as an ultrasound probe.

The computing device 101 may render images at the display device 110, via the display interface 112. The display device 110 may an integrated component of the computing device 101, a remote component such as an external monitor, or any other configuration enabling the computing device 101 to render a graphical user interface. As discussed in more detail below, a graphical user interface rendered at the display device 110 may be used in cine-loop adjustments.

The block diagram of FIG. 1 is not intended to indicate that the computing device 101 is to include all of the components shown in FIG. 1. Further, the computing device 101 may include any number of additional components not shown in FIG. 1, depending on the details of the specific implementation.

Figure 2:
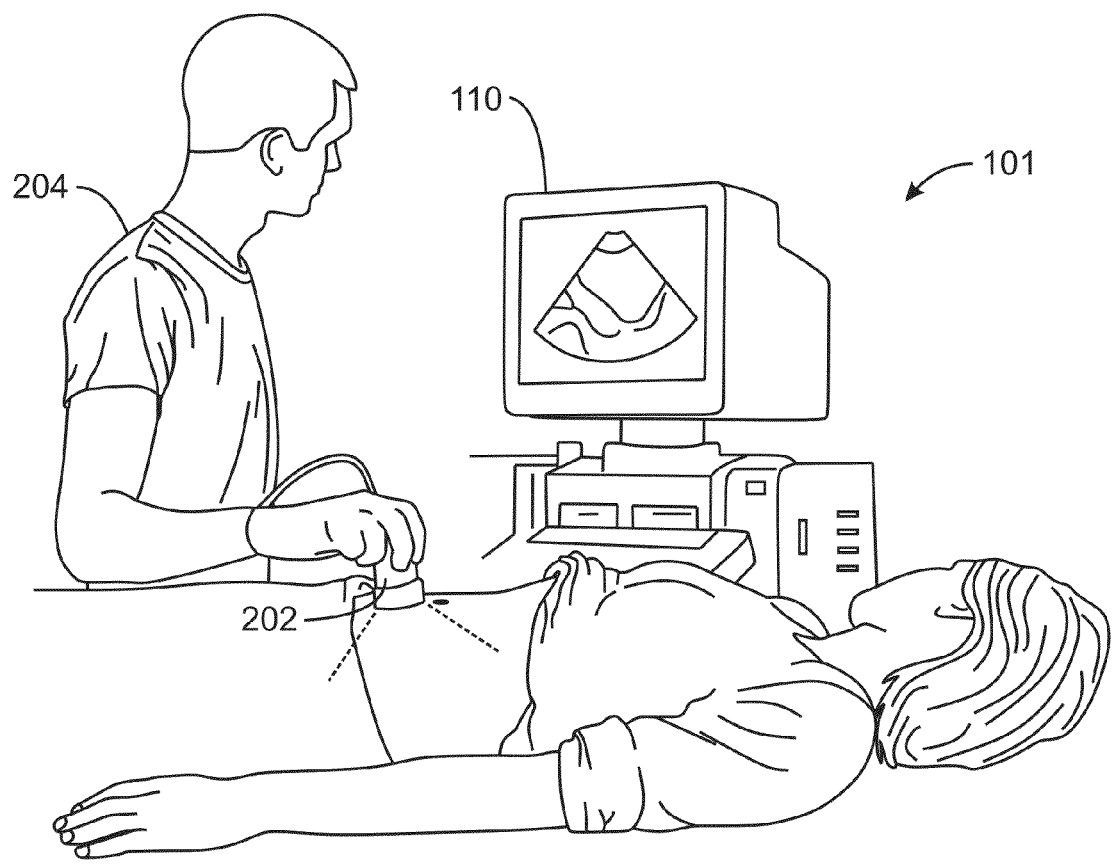
FIG. 2 illustrates a diagram of an environment for adjusting a cine-loop.

FIG. 2 illustrates a diagram of an environment for adjusting a cine-loop. As discussed above, an imaging device, such as one of the imaging devices 114 of FIG. 1, may include an ultrasound probe 202. In some cases, the ultrasound probe 202 may be a four-dimensional probe configured to capture 30 to 50 volumes per second. Four-dimensional image data includes three-dimensional volumes over a given period of time. The image data may be stored on the computing device 101. Although not illustrated in FIG. 2, in some cases, the image data is transmitted over a network to be stored in a centralized computer. In any case, a user 204 may be a person trained to use the ultrasound probe 202, such as a physician, a medical technician, and the like.

As illustrated in FIG. 2, the display 110 of the computing device 101 displays the image data as it is being captured. A given set of image data including volumes may be saved for later stitching and analysis. The stitching may generate a cine-loop as described in more detail below.

Figure 3:
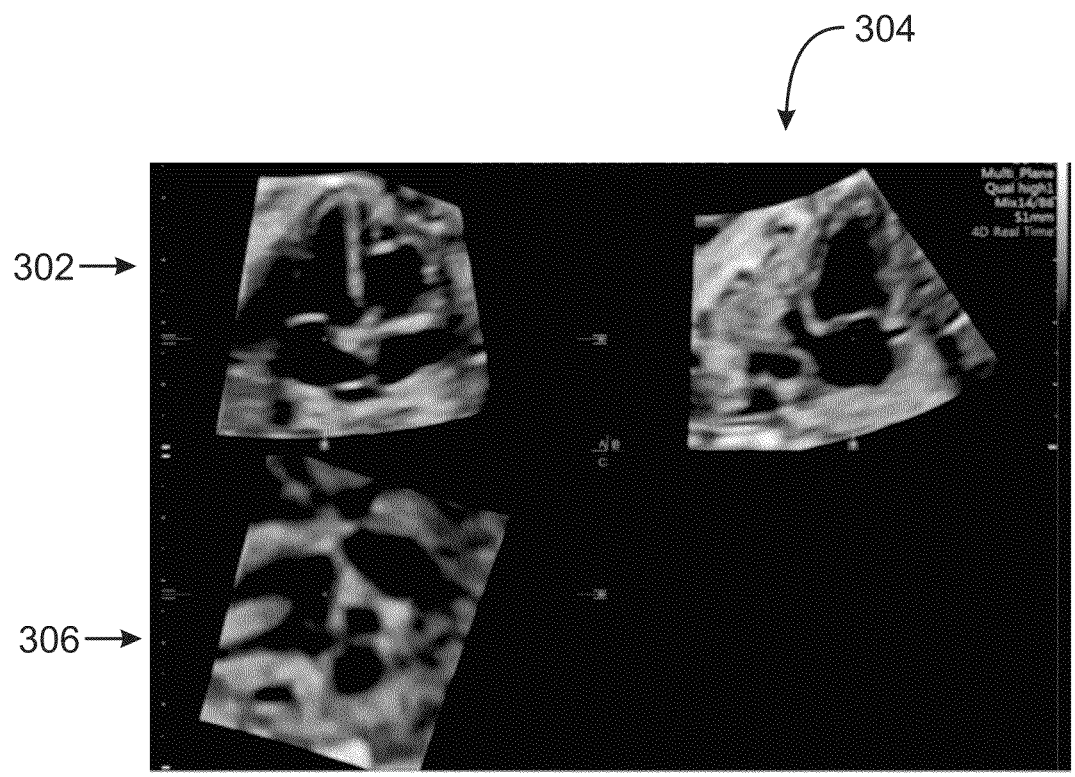
FIG. 3 is a diagram illustrating a three dimensional ultrasound image.

FIG. 3 is a diagram illustrating a three dimensional ultrasound image. As discussed above in regard to FIG. 2, the image data may be three dimensional volumes wherein the fourth dimension is time. Although not illustrated in FIG. 3, image data captured 300 may be a moving video clip. The video clip may include a view from a first perspective 302, a view from a second perspective 304 that is orthogonal to the first perspective 302, and a view from a third perspective 306 that is orthogonal to both the first perspective 302 and the second perspective 304.

As discussed above, the video clip may be used to generate a cine-loop. In some embodiments, the cine-loop will be automatically generated based on relative positions of moving components of the video clip such that the cine-loop captures one heartbeat without a stitching artifact. In other embodiments, the cine-loop may need to be adjusted, as discussed in more detail below.

Figure 4:
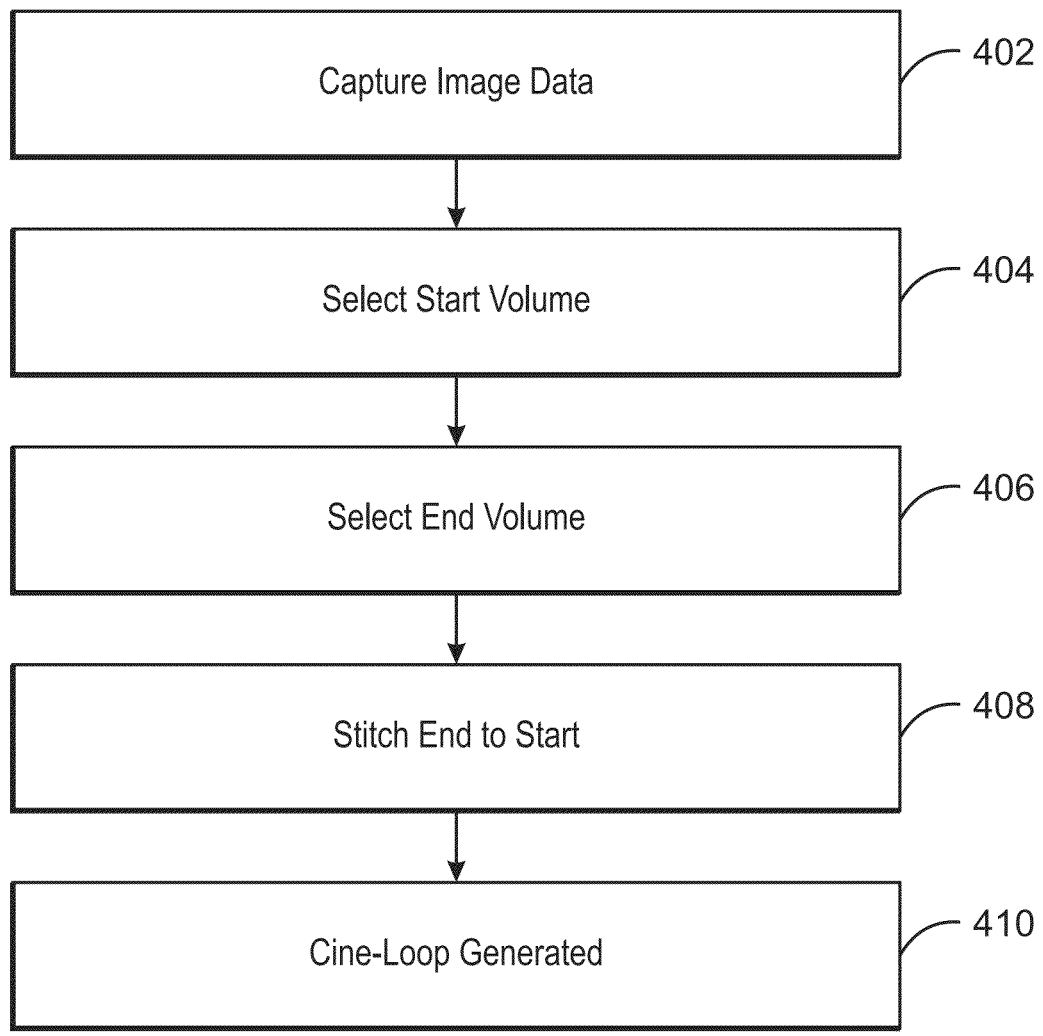
FIG. 4 is a flow diagram of a process of generating a cine-loop.

FIG. 4 is a flow diagram of a process of generating a cine-loop. At 402, image data is captured. As discussed above, the image capture data may be a four dimensional ultrasound. At 404, a start volume is selected. The start volume may be selected 404 by a user, such as the user 202. In embodiments, the start volume is selected by identifying a beginning of a heart contraction, or the beginning of a systole period. At 406, an end volume is selected. In embodiments, the end volume is selected by determining an average time period associated with a heartbeat.

For example, if the heart being imaged is a fetal heart averaging beats 120 times in one minute, one heart beat can be determined to have a time period of about 0.5 seconds. In some scenarios, the average heart rate is predetermined data. In other scenarios, the average heart rate may be measured data. In any case, at 408, the end volume is stitched to the start volume to generate a cine-loop at 410.

The cine-loop generated at 410 may include stitching artifacts. The stitching artifact may be the result of the cine-loop being either too long or too short in comparison to the time period of the actual heartbeat of the heart at least partially captured in the cine-loop. Although not illustrated in FIG. 4, the stitching artifact may appear as a jump in the cine-loop since the cine-loop captures either too little image data or too much image data as a result of the inaccurate length of the cine-loop. Therefore, the cine-loop length can be adjusted to reduce or eliminate the stitching artifact.

Figure 5:
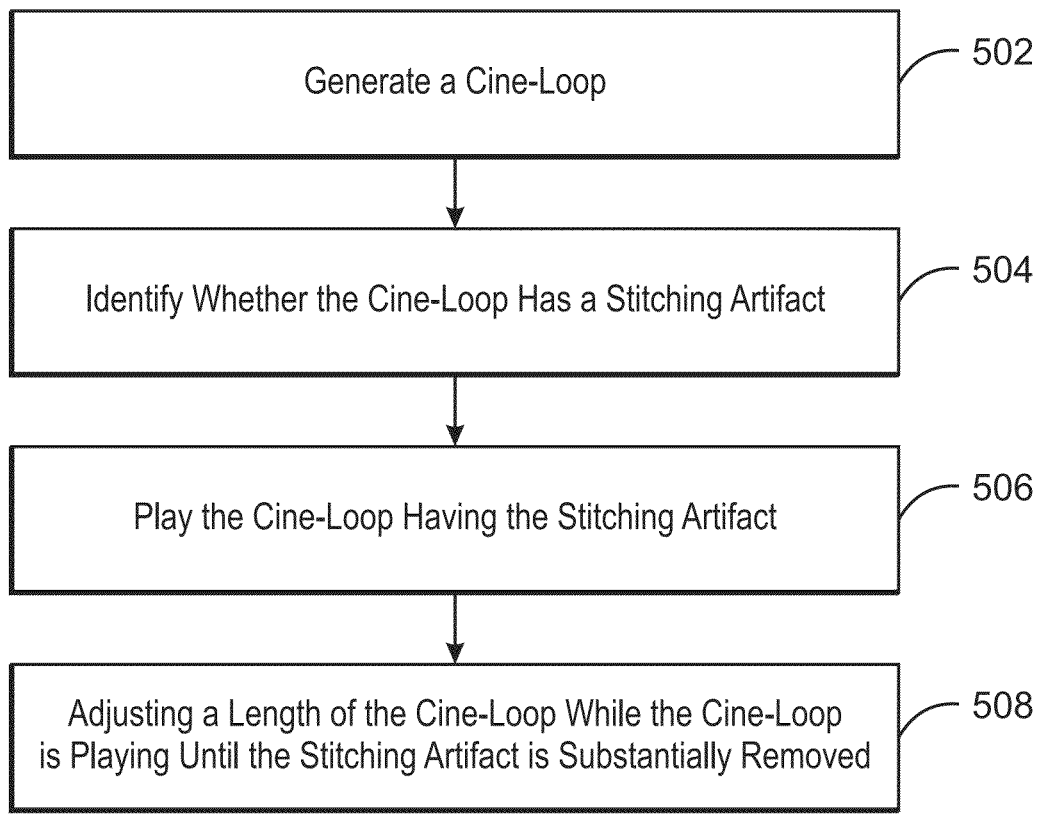
FIG. 5 is a block diagram illustrating a method of for adjusting a cine-loop.

FIG. 5 is a block diagram illustrating a method of for adjusting a cine-loop. At block 502, the cine-loop may be generated. In embodiments, the cine-loop is generated according to the techniques discussed above in regard to FIG. 4. At block 504, method 500 includes identifying whether the cine-loop has a stitching artifact. If the cine-loop includes a stitching artifact, the cine-loop is played at 506. While the cine-loop is playing, a length of the cine-loop is adjusted until the stitching artifact is substantially removed.

The method 500 described above in regard to FIG. 5 enables a cine-loop to be adjusted while being played. The adjustments may be rendered at a display device as the adjustments are made to the cine-loop length. By enabling a user to play the cine-loop at 506 while concurrently adjusting the length of the cine-loop, time and effort required to adjust the cine-loop length may be reduced. Specifically, rather than adjusting the cine-loop length at a different time, or non-currently with the cine-loop playing, the techniques described herein enable a user to tune the length of the cine-loop by viewing the cine-loop as the length is adjusted. Once the user identifies that a stitching artifact has been substantially reduced or removed, the user may archive and/or analyze the heart cycle.

In some scenarios, the length of the cine-loop is adjusted such that the cine-loop ends before another heart contraction begins. Further, the length of the cine-loop may be adjusted such that the cine-loop ends after an entire diastole period following the heart contraction associated with the selected starting volume.

Figure 6:
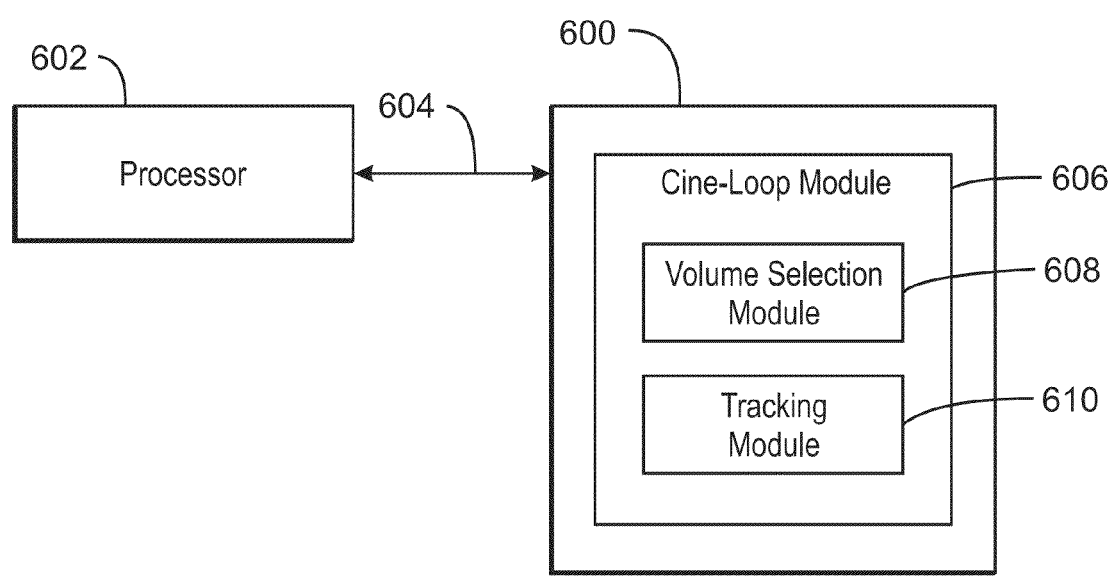
FIG. 6 is a block diagram of a computer readable medium that includes a module for generating a cine-loop.

FIG. 6 is a block diagram of a computer readable medium that includes a module for generating a cine-loop. The computer readable medium 600 may be a non-transitory computer readable medium, a storage device configured to store executable instructions, or any combination thereof. In any case, the computer-readable medium is not configured as a carry wave or a signal.

The computer-readable medium 600 includes code adapted to direct a processor 602 to perform actions. The processor 602 accesses modules over a system bus 604.

A cine-loop module 606 may be configured to generate a cine-loop wherein a cine-loop length is automatically determined to substantially remove a stitching artifact. In other words, the cine-loop generated by the cine-loop module 606 may automatically generate a cine-loop capturing an entire heartbeat—nothing more and nothing less.

The cine-loop module 606 may include sub-modules including a volume selection module 608 and a tracking module 610. The volume selection module 608 may be configured to identify a start volume of four-dimensional image capture of a beating heart. The start volume may be identified as the beginning of a systole period. The tracking module 610 may identify a location of a moving component of the heart. For example, the tracking module 610 may identify a component, such as ventricle, a valve, or any other component that moves in a period based on the heartbeat period. The tracking module 610 may determine when the moving component returns to the identified location, whereupon the volume selection module 608 selects a stop volume. In some scenarios, tracking module 610 is configured to allow the moving component to return to the identified location a predetermined number of times, specific to the type of moving object and the expected movement of the moving object within the heartbeat.

In some cases, the automatic cine-loop generated by the cine-loop module 606 may be adjusted by a user. For example, the cine-loop may be played, and, as discussed above in regard to FIG. 5, the length of the cine-loop may be adjusted while the cine-loop is playing. In this scenario, an automatically generated cine-loop may be augmented as desired by a user.

While the detailed drawings and specific examples given describe particular embodiments, they serve the purpose of illustration only. The systems and methods shown and described are not limited to the precise details and conditions provided herein. Rather, any number of substitutions, modifications, changes, and/or omissions may be made in the design, operating conditions, and arrangements of the embodiments described herein without departing from the spirit of the present techniques as expressed in the appended claims.

This written description uses examples to disclose the techniques described herein, including the best mode, and also to enable any person skilled in the art to practice the techniques described herein, including making and using any devices or systems and performing any incorporated methods. The patentable scope of the techniques described herein is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for adjusting a cine-loop, comprising:
    generating a cine-loop by selecting a start frame, selecting an end frame and stitching the end frame to the start frame;
    identifying whether the cine-loop has a stitching artifact; and, if so
    playing the cine-loop having the stitching artifact; and
    adjusting a length of the cine-loop while the cine-loop is playing by adjusting at least one of the start frame and the end frame until the stitching artifact is substantially removed.

2. The method of claim 1, wherein the cine-loop is adjusted to capture a single heartbeat, and wherein the stitching artifact is based on a cine-length that is either too short or too long in comparison to a period of the single heartbeat.

3. The method of claim 2, wherein the generating a cine-loop comprises:
    generating a cine-loop having a motion artifact, wherein a motion artifact is a result of movement of an imaged object during image capture; and
    adjusting the start frame of the cine-loop while the first cine-loop is playing until the motion artifact is substantially reduced.

4. The method of claim 2, wherein the start frame comprises a starting volume associated with a beginning of a heart contraction and the end frame comprises an ending volume based on the average time for one heartbeat, and generating the cine-loop comprises:

stitching the ending volume to the starting volume to create a four dimensional image capture loop of the heartbeat.

5. The method of claim 4, wherein the length of the cine-loop is adjusted such that the cine-loop ends before another heart contraction begins.

6. The method of claim 4, wherein the cine-loop is adjusted such that the cine-loop ends after an entire diastole period following the heart contraction associated with the selected starting volume.

7. The method of claim 1, wherein the cine-loop comprises one or more of:
   a four dimensional image capture;
   a two dimensional image capture;
   a two-dimensional image capture comprising Doppler image data;
   a four-dimensional image capture comprising Doppler image data; or
   any combination thereof.

8. A system for adjusting a cine-loop, comprising:
   a processing device; and
   an adjustment module comprising logic, at least partially comprising hardware logic to:
      generate a cine-loop by stitching an end frame to a start frame;
      identify whether the cine-loop has a stitching artifact; and, if so
      play the cine-loop having the stitching artifact; and
      adjust a length of the cine-loop while the cine-loop is playing by adjusting at least one of the start frame and the end frame until the stitching artifact is substantially removed.

9. The system of claim 8, wherein the cine-loop is adjusted to capture a single heartbeat, wherein the stitching artifact is based on a cine-length that is either too short or too long in comparison to a period of the single heartbeat, and wherein the cine-loop having the stitching artifact is identified based on a cine-length generating a jump within the cine-loop when the cine-loop is played.

10. The system of claim 9, wherein the generating a cine-loop comprises:
   generating a cine-loop having a motion artifact, wherein a motion artifact is a result of movement of an imaged object during image capture; and
   adjusting the start frame of the cine-loop while the first cine-loop is playing until the motion artifact is substantially reduced.

11. The system of claim 9, wherein the adjustment module is configured to:
   identify the start frame by selecting a starting volume associated with a beginning of a heart contraction;
   identify the end frame by selecting an ending volume based on the an average time for one heartbeat; and
   generate the cine-loop by stitching the ending volume to the starting volume to create a four dimensional image capture loop of the heartbeat.

12. The system of claim 11, wherein the length of the cine-loop is adjusted such that the cine-loop ends before another heart contraction begins.

13. The system of claim 11, wherein the cine-loop is adjusted such that the cine-loop ends after an entire diastole period following the heart contraction associated with the selected starting volume.

14. The system of claim 8, wherein the cine-loop is a four dimensional image capture.

15. A computer-readable medium for generating a cine-loop, the computer-readable medium comprising processor-executable code to:
   generate a cine-loop by identifying a start frame, identifying an end frame and stitching the end frame to the start frame; and
   wherein the cine-loop is generated by automatically determining a cine-loop length to substantially remove a stitching artifact.

16. The computer-readable medium of claim 15, wherein the cine-loop is a capture of a single heartbeat, the start frame comprises a start volume and the end frame comprises a stop volume, and wherein the cine-loop length is determined by:
   identifying the start volume;
   identifying a location of a moving component of a heart generating the heartbeat;
   determining when the moving component returns to the identified location; and
   selecting the stop volume based on when the moving component returns to the identified location.

17. The computer-readable medium of claim 15, further comprising processor-executable code to enable a user to play the cine-loop having the stitching artifact.

18. The computer-readable medium of claim 17, further comprising processor-executable code to enable a user to adjust a length of the cine-loop while the cine-loop is playing until the stitching artifact is substantially removed.

19. The computer-readable medium of claim 17, wherein the stitching artifact is identified based on a cine-length generating a jump within cine-loop when the cine-loop is played.

20. The computer-readable medium of claim 15, wherein the generating a cine-loop comprises:
   generating a cine-loop having a motion artifact, wherein a motion artifact is a result of movement of an imaged object during image capture; and
   adjusting the start frame of the cine-loop while the first cine-loop is playing until the motion artifact is substantially reduced.

* * * * *